(12) United States Patent
Kashiwagi et al.

(10) Patent No.: US 11,970,694 B2
(45) Date of Patent: Apr. 30, 2024

(54) RAPID DISPLAY METHOD IN TRANSLATIONAL SYNTHESIS OF PEPTIDE

(71) Applicant: PeptiDream Inc., Kanagawa (JP)

(72) Inventors: Kenji Kashiwagi, Tokyo (JP); Patrick Reid, Tokyo (JP)

(73) Assignee: PeptiDream Inc., Kanagawa (JP)

( * ) Notice: Subject to any disclaimer, the term of this patent is extended or adjusted under 35 U.S.C. 154(b) by 860 days.

(21) Appl. No.: 16/807,435

(22) Filed: Mar. 3, 2020

(65) Prior Publication Data
US 2020/0199579 A1 Jun. 25, 2020

Related U.S. Application Data

(63) Continuation of application No. 13/502,487, filed as application No. PCT/JP2010/068549 on Oct. 21, 2010, now abandoned.

(30) Foreign Application Priority Data

Oct. 22, 2009 (JP) ................ 2009-243240

(51) Int. Cl.
*C12N 15/10* (2006.01)
*C40B 40/08* (2006.01)
*C40B 50/06* (2006.01)

(52) U.S. Cl.
CPC .......... *C12N 15/1062* (2013.01); *C40B 40/08* (2013.01); *C40B 50/06* (2013.01)

(58) Field of Classification Search
CPC ...... C12N 15/1062; C40B 40/08; C40B 50/06
See application file for complete search history.

(56) References Cited

U.S. PATENT DOCUMENTS

| | | | |
|---|---|---|---|
| 6,361,943 B1 | 3/2002 | Yanagawa et al. | |
| 7,270,950 B2 | 9/2007 | Szostak et al. | 435/6.11 |
| 2004/0018536 A1 | 1/2004 | Yanagawa et al. | 435/6 |
| 2008/0058217 A1* | 3/2008 | Szostak | C12N 15/1062 506/9 |
| 2008/0312103 A1* | 12/2008 | Nemoto | C12N 15/1062 506/17 |
| 2009/0156416 A1 | 6/2009 | Tan et al. | 506/9 |

FOREIGN PATENT DOCUMENTS

WO WO 98/16636 A1 4/1998
WO WO 98/31700 A1 7/1998

OTHER PUBLICATIONS

Niwa et al. (2009) A flexizyme that selectively charges amino acids activated by a water-friendly leaving group. Bioorganic & Medicinal Chemistry Letters, 19:3892-3894 (Year: 2009).*
Craig et al. (1992) Plasmid cDNA-directed protein synthesis in a coupled eukaryotic in vitro transcription-translation system. Nucleic Acids Research, 20(19):4987-4995 (Year: 1992).*
Kurz et al. (2000) Psoralen photo-crosslinked mRNA-puromycin conjugates: a novel template for the rapid and facile preparation of mRNA-protein fusions. Nucleic Acids Research, 28(18):e83,pp. i-v.
Nelson et al. "Lehninger Principles of Biochemistry, 4th ed". New York:W. H. Freeman and Company, 2005, p. 1049-1053.
Monro et al. (1968) Ribosome-catalyzed Peptidyl Transfer: Substrate Specificity at the P-Site. Biochemistry, 61:1042-1049.
Niwa et al. (2009) A flexizyme that selectively charges amino acids activated by a water-friendly leaving group. Bioorganic & Medicinal Chemistry Letters, 19:3892-3894.
Tamura et al.Proceedings of the National Academy of Sciences 98.4 (2001): 1393-1397.
Extended European Search Report for European Application No. 10825006.9 dated Jul. 18, 2013.
Kurz, Markus et al., "cDNA—Protein Fusions: Covalent Protein—Gene Conjugates For The In Vitro Selection Of Peptides And Proteins", Chembiochem—A European Journal of Chemical Biology, vol. 2, No. 9, Sep. 3, 2001, pp. 666-672, XP002415941.
Miyamoto-Sato, Etsuko and Yanagawa, Hiroshi, "Puromycin Technology For In Vitro Evolution And Proteome Exploration", Viva Origino vol. 34, No. 4, Dec. 2006, pp. 148-154, XP002699813.
Niwa, Nobuyoshi et al., "A Flexizyme That Selectively Charges Amino Acids Activated By A Water-friendly Leaving Group" Bioorganic & Medicinal Chemistry Letters, vol. 19, No. 14, Jul. 15, 2009, pp. 3892-3894, XP002699326.
Murikami et al. Nucleic Acids Symp Ser (Nov. 2006) 50 (1): 35-36.
Moroder et al. Angew. Chem. Int. Ed. 2009, 48, 4056-4060.
Weigand et al. Chemistry and Biology, Sep. 1997, 4: 675-683.
Nemoto et al., "In vitro virus: Bonding of mRNA bearing puromycin at the 3"-terminal and to the C-terminal end of its encoded protein on the ribosome in vitro," FEBS Letters (1997), vol. 414, pp. 405-408.
Ohuchi et al., "The flexizyme system: a highly flexible tRNA aminoacylation tool for the translation apparatus." Curr. Opin. Chem. Biol. (2007), vol. 11, pp. 537-542.
Ramaswamy et al., "Designer Ribozymes: Programming the tRNA Specificity into Flexizyme," J. Am. Chem. Soc. (2004), vol. 126, pp. 11454-11455.
Roberts and Szostak, "RNA-peptide fusions for the in vitro selection of peptides and proteins," Proc. Natl. Acad. Sci. USA (Nov. 1997), vol. 94, pp. 12297-12302.

(Continued)

*Primary Examiner* — Abigail Vanhorn
*Assistant Examiner* — Morgan T Lindgren Baltzell
(74) *Attorney, Agent, or Firm* — Suzannah K. Sundby, Esq.; Canady + Lortz LLP

(57) ABSTRACT

Provided are linkers suitable for preparing a conjugate of a nucleic acid and a peptide as a translation product thereof in a reconstituted cell-free translation system in genotype-phenotype mapping (display methods), said linkers comprising a single-stranded structure region having a side chain base pairing with the base at the 3'-end of an mRNA at one end and a peptidyl acceptor region containing an amino acid attached to an oligo RNA consisting of a nucleotide sequence of ACCA via an ester bond at the other end, characterized in that the ester bond is formed by using an artificial RNA catalyst. Also provided are display methods using [mRNA]-[linker]-[peptide] conjugates assembled via such linkers.

9 Claims, 5 Drawing Sheets

Specification includes a Sequence Listing.

(56) References Cited

OTHER PUBLICATIONS

Shimizu et al., "Cell-free translation reconstituted with purified components;" Nature Biotechnology (Aug. 2001), vol. 19, pp. 751-755.

Yamaguchi et al., "cDNA display: a novel screening method for functional disulfide-rich peptides by solid-phase synthesis and stabilization of mRNA-protein fusions," Nucleic Acids Research (2009), vol. 37, No. 16, e108, pp. 1-13.

\* cited by examiner

Puromycin conjugated linker
(tyrosyl-tRNA analog)

SEQUENCE LISTING

```
<160> NUMBER OF SEQ ID NOS: 25

<210> SEQ ID NO 1
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 1
ctcccgcccc ccgtcc                                                       16

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
cccgcctccc gcccccgtc c                                                  21

<210> SEQ ID NO 3
<211> LENGTH: 45
<212> TYPE: RNA
<213> ORGANISM: Artificial Sequence
<220> FEATURE:
<223> OTHER INFORMATION: Flexizyme Fx

<400> SEQUENCE: 3
ggaucgaaag auuuccgcag gcccgaaagg guauuggcgu uaggu                       45
```

```
<210> SEQ ID NO 4
<211> LENGTH: 45
<212> TYPE: RNA
<213> ORGANISM: Artificial Sequence
<220> FEATURE:
<223> OTHER INFORMATION: Flexizyme eFx

<400> SEQUENCE: 4
ggaucgaaag auuccgcgg ccccgaaagg ggauuagcgu uaggu            45

<210> SEQ ID NO 5
<211> LENGTH: 46
<212> TYPE: RNA
<213> ORGANISM: Artificial Sequence
<220> FEATURE:
<223> OTHER INFORMATION: Flexizyme dFx

<400> SEQUENCE: 5
ggaucgaaag auuccgcau ccccgaaagg guacauggcg uuaggu           46

<210> SEQ ID NO 6
<211> LENGTH: 17
<212> TYPE: DNA
<213> ORGANISM: Artificial Sequence
<220> FEATURE:
<223> OTHER INFORMATION: synthetic oligonucletide

<400> SEQUENCE: 6
taatacgact cactata                                          17

<210> SEQ ID NO 7
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 7
gggttaactt taagaaggag atatacat                              28

<210> SEQ ID NO 8
<211> LENGTH: 66
<212> TYPE: DNA
<213> ORGANISM: Artificial Sequence
<220> FEATURE:
<223> OTHER INFORMATION: synthetic oligonucleotide TNF-a D-Trp.R66

<400> SEQUENCE: 8
gccgctgccg ctgccgcaat gcttcagata cagacaatgc agacgttgca tatgtatatc   60
tccttc                                                             66

<210> SEQ ID NO 9
<211> LENGTH: 63
<212> TYPE: DNA
<213> ORGANISM: Artificial Sequence
<220> FEATURE:
<223> OTHER INFORMATION: synthetic oligonucleotide EMP1SS.F63

<400> SEQUENCE: 9
gaaggagata tacatatggc agcaggtggt acctattctt ctcattttgg tccgctgacc   60
tgg                                                                63

<210> SEQ ID NO 10
<211> LENGTH: 63
<212> TYPE: DNA
```

-continued

```
<213> ORGANISM: Artificial Sequence
<220> FEATURE:
<223> OTHER INFORMATION: synthetic oligonucleotide EMP1SS.R63

<400> SEQUENCE: 10
gccgctgccg ctgccgcatg ctgcaccacc ttgcggctta gaaacccagg tcagcggacc    60
aaa                                                                   63

<210> SEQ ID NO 11
<211> LENGTH: 48
<212> TYPE: DNA
<213> ORGANISM: Artificial Sequence
<220> FEATURE:
<223> OTHER INFORMATION: synthetic oligonucleotide T7g10M.F48

<400> SEQUENCE: 11
taatacgact cactataggg ttaactttaa gaaggagata tacatatg                  48

<210> SEQ ID NO 12
<211> LENGTH: 39
<212> TYPE: DNA
<213> ORGANISM: Artificial Sequence
<220> FEATURE:
<223> OTHER INFORMATION: synthetic oligonucleotide CGS3an13.R39

<400> SEQUENCE: 12
tttccgcccc ccgtcctagc tgccgctgcc gctgccgca                            39

<210> SEQ ID NO 13
<211> LENGTH: 44
<212> TYPE: DNA
<213> ORGANISM: Artificial Sequence
<220> FEATURE:
<223> OTHER INFORMATION: synthetic oligonucleotide CGS3an21.R44

<400> SEQUENCE: 13
cccgcctccc gcccccgtc ctagctgccg ctgccgctgc cgca                       44

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide CGSan13.R21

<400> SEQUENCE: 14
tagctgccgc tgccgctgcc g                                               21

<210> SEQ ID NO 15
<211> LENGTH: 122
<212> TYPE: DNA
<213> ORGANISM: Artificial Sequence
<220> FEATURE:
<223> OTHER INFORMATION: TNF-alfa-DW(an21)

<400> SEQUENCE: 15
taatacgact cactataggg ttaactttaa gaaggagata tacatatgca acgtctgcat     60
tgtctgtatc tgaagcattg cggcagcggc agcggcagct aggacggggg gcgggaggcg    120
gg                                                                  122

<210> SEQ ID NO 16
<211> LENGTH: 117
<212> TYPE: DNA
<213> ORGANISM: Artificial Sequence
```

<220> FEATURE:
<223> OTHER INFORMATION: TNF-alfa-DW(an13)

<400> SEQUENCE: 16
taatacgact cactataggg ttaactttaa gaaggagata tacatatgca acgtctgcat    60
tgtctgtatc tgaagcattg cggcagcggc agcggcagct aggacggggg gcggaaa      117

<210> SEQ ID NO 17
<211> LENGTH: 164
<212> TYPE: DNA
<213> ORGANISM: Artificial Sequence
<220> FEATURE:
<223> OTHER INFORMATION: EMP1SS(an21)

<400> SEQUENCE: 17
taatacgact cactataggg ttaactttaa gaaggagata tacatatggc agcaggtggt    60
acctattctt ctcattttgg tccgctgacc tgggtttcta agccgcaagg tggtgcagca   120
tgcggcagcg gcagcggcag ctaggacggg gggcgggagg cggg                    164

<210> SEQ ID NO 18
<211> LENGTH: 183
<212> TYPE: PRT
<213> ORGANISM: Artificial Sequence
<220> FEATURE:
<223> OTHER INFORMATION: TNF-alfa

<400> SEQUENCE: 18

Met Ser Gly Leu Asn Asp Ile Phe Glu Ala Gln Lys Ile Glu Trp His
1               5                   10                  15

Glu Gly His His His His His His Gly Ser Val Arg Ser Ser Ser Arg
            20                  25                  30

Thr Pro Ser Asp Lys Pro Val Ala His Val Val Ala Asn Pro Gln Ala
        35                  40                  45

Glu Gly Gln Leu Gln Trp Leu Asn Arg Arg Ala Asn Ala Leu Leu Ala
    50                  55                  60

Asn Gly Val Glu Leu Arg Asp Asn Gln Leu Val Val Pro Ser Glu Gly
65                  70                  75                  80

Leu Tyr Leu Ile Tyr Ser Gln Val Leu Phe Lys Gly Gln Gly Cys Pro
                85                  90                  95

Ser Thr His Val Leu Leu Thr His Thr Ile Ser Arg Ile Ala Val Ser
            100                 105                 110

Tyr Gln Thr Lys Val Asn Leu Leu Ser Ala Ile Lys Ser Pro Cys Gln
        115                 120                 125

Arg Glu Thr Pro Glu Gly Ala Glu Ala Lys Pro Trp Tyr Glu Pro Ile
    130                 135                 140

Tyr Leu Gly Gly Val Phe Gln Leu Glu Lys Gly Asp Arg Leu Ser Ala
145                 150                 155                 160

Glu Ile Asn Arg Pro Asp Tyr Leu Asp Phe Ala Glu Ser Gly Gln Val
                165                 170                 175

Tyr Phe Gly Ile Ile Ala Leu
            180

<210> SEQ ID NO 19
<211> LENGTH: 47
<212> TYPE: RNA
<213> ORGANISM: Artificial Sequence
<220> FEATURE:
<223> OTHER INFORMATION: Flexizyme aFx

```
<400> SEQUENCE: 19
ggaucgaaag auuccgcac ccccgaaagg gguaaguggc guuaggu          47

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Cys Gly Ser Gly Ser Gly Ser
1               5

<210> SEQ ID NO 21
<211> LENGTH: 25
<212> TYPE: DNA
<213> ORGANISM: Artificial Sequence
<220> FEATURE:
<223> OTHER INFORMATION: Synthetic chimeric DNA/RNA oligonucleotide:
      an21-ACCA
<220> FEATURE:
<221> NAME/KEY: misc_feature
<222> LOCATION: (21)..(22)
<223> OTHER INFORMATION: Location of Spacer18 (hexaethylene glycol)
<220> FEATURE:
<221> NAME/KEY: misc_feature
<222> LOCATION: (22)..(25)
<223> OTHER INFORMATION: RNA

<400> SEQUENCE: 21
cccgcctccc gcccccgtc cacca                                 25

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide: AviTag sequence

<400> SEQUENCE: 22

Gly Leu Asn Asp Ile Phe Glu Ala Gln Lys Ile Glu Trp His Glu
1               5                   10                  15

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide: Hisx6 tag sequence

<400> SEQUENCE: 23

His His His His His His
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic TNF-alpha-DW peptide aptamer
<220> FEATURE:
<221> NAME/KEY: misc_feature
<222> LOCATION: (1)..(1)
<223> OTHER INFORMATION: Xaa can be any naturally occurring amino acid
```

```
<400> SEQUENCE: 24

Xaa Gln Arg Leu His Cys Leu Tyr Leu Lys His
1               5                   10

<210> SEQ ID NO 25
<211> LENGTH: 25
<212> TYPE: PRT
<213> ORGANISM: Artificial Sequence
<220> FEATURE:
<223> OTHER INFORMATION: Synthetic peptide: EMP1SS
<220> FEATURE:
<221> NAME/KEY: misc_feature
<222> LOCATION: (1)..(1)
<223> OTHER INFORMATION: Xaa is Ac-D-Trp

<400> SEQUENCE: 25

Xaa Ala Ala Gly Gly Thr Tyr Ser Ser His Phe Gly Pro Leu Thr Trp
1               5                   10                  15

Val Ser Lys Pro Gln Gly Gly Ala Ala
            20                  25
```

RAPID DISPLAY METHOD IN TRANSLATIONAL SYNTHESIS OF PEPTIDE

CROSS-REFERENCE TO RELATED APPLICATIONS

This application is a continuation of U.S. Ser. No. 13/502,487 filed Apr. 17, 2012, which is herein incorporated by reference in its entirety; U.S. Ser. No. 13/502,487 is a National Stage Entry of PCT/JP2010/068549 filed Oct. 21, 2010, which claims priority to JP 2009-243240 filed Oct. 22, 2009.

REFERENCE TO A SEQUENCE LISTING SUBMITTED VIA EFS-WEB

The content of the ASCII text file of the sequence listing named "20230627_101620_002CON1_seq" which is 8,035 bytes in size was created on Jun. 27, 2023 and electronically submitted via EFS-Web on Jul. 3, 2023 is incorporated herein by reference in its entirety.

TECHNICAL FIELD

The present invention relates to a novel method used for preparing a conjugate of a cDNA or mRNA and a peptide or protein translated therefrom in genotype-phenotype mapping (display systems). This method was designated as RAPID display method by us. This method is suitable for screening peptide aptamers as potential drug candidates from unusual peptide libraries constructed using the previously reported flexizyme system (or RAPID system: Random Peptide Integrated Discovery system).

BACKGROUND ART

Technologies for mapping genotype and phenotype, also known as display methods, were born as tools for evolutionary molecular engineering, and include various known methods such as mRNA display ("in vitro virus", Nemoto N. et al. FEBS Lett. 414, 405-408 (1997), International Publication WO98/16636; or "RNA-peptide fusions", Roberts, R. W. & Szostak, J. W., Proc. Natl. Acad. Sci. USA., 94, 12297-12302 (1997), International Publication WO98/31700), STABLE (non-covalent DNA display), microbead/droplet display, covalent DNA display, phage display, ribosome display, etc. Display methods are useful for selecting genetic information of a polypeptide having a specific function because a gene corresponding to a functional peptide or protein molecule selected from a library is conjugated to such a molecule so that the sequence thereof can be readily read.

mRNA display is a technique for linking genotype and phenotype by covalently coupling an mRNA as genotype and a peptide molecule as phenotype using a cell-free translation system (in vitro protein synthesis system), and currently applied by coupling a synthesized peptide molecule and an mRNA encoding it via puromycin, which is an analogue of the 3' end of a tyrosyl-tRNA.

In mRNA display, an mRNA containing puromycin preliminarily attached to its 3' end via a suitable linker is introduced into a cell-free translation system to synthesize a peptide from the mRNA so that the puromycin is fused to the C-terminus of a growing peptide chain as a substrate for peptidyl transfer reaction on a ribosome and the translated peptide molecule is fused to the mRNA via the puromycin (FIG. 1A). The linker is inserted between the mRNA and the puromycin mainly for the purpose of efficiently incorporating the puromycin into the A site of the ribosome. Puromycin is characterized in that the adenosine-like moiety and the amino acid (tyrosine)-like moiety form an amide bond rather than an ester bond, unlike the 3' end of an aminoacyl-tRNA (FIG. 1B). Thus, the conjugate of the puromycin and the peptide fused to each other on the ribosome is resistant to hydrolysis and stable.

In mRNA display, it is necessary to attach puromycin to the 3' end of the mRNA in advance outside the cell-free translation system in order to couple the mRNA and the translation product via the puromycin. This attachment takes place by either first preparing a puromycin-conjugated linker having a spacer consisting of a linear polymer synthesized at the 5' end from puromycin and then fusing the linker to the 3' end of the mRNA or conjugating a spacer to the 3' end of the mRNA and then fusing the puromycin to the conjugate. In either method, the linear polymer spacer typically contains a phosphate group or nucleotide at an end, and the linkage between the 3' end of the mRNA and the 5' end of the linker is a covalent bond via the phosphate group. This covalent bond is formed by a reaction using an RNA ligase or DNA ligase or a standard organic chemistry reaction.

CITATION LIST

Patent Documents

Patent document 1: Japanese Patent No. 3683282 (International Publication WO98/16636)
Patent document 2: Japanese Patent No. 3683902
Patent document 3: Japanese Patent No. 3692542 (International Publication WO98/31700)

Non-Patent Documents

Non-patent document 1: Nemoto N. et al. FEBS Lett. 414, 405-408 (1997)
Non-patent document 2: Roberts, R. W. & Szostak, J. W., Proc. Natl. Acad. Sci. USA., 94, 12297-12302 (1997)

SUMMARY OF INVENTION

Technical Problems

In known mRNA display methods, an mRNA template having puromycin at the 3' end is added to a cell-free translation system using wheat germ extract or rabbit reticulocyte lysate to translate it into a peptide. Thus, it is necessary to carry out transcription from DNA into mRNA and fusion reaction between mRNA and puromycin in advance outside the translation system.

Recently, reconstituted cell-free translation systems were developed by individually purifying and mixing elements necessary for translation in systems using *E. coli* ribosomes (H. F. Kung, B. Redfield, B. V. Treadwell, B. Eskin, C. Spears and H. Weissbach (1977) "DNA-directed in vitro synthesis of beta-galactosidase. Studies with purified factors" The Journal of Biological Chemistry Vol. 252, No. 19, 6889-6894; M. C. Gonza, C. Cunningham and R. M. Green (1985) "Isolation and point of action of a factor from *Escherichia coli* required to reconstruct translation" Proceeding of National Academy of Sciences of the United States of America Vol. 82, 1648-1652; M. Y. Pavlov and M. Ehrenberg (1996) "Rate of translation of natural mRNAs in an optimized in vitro system" Archives of Biochemistry and Biophysics Vol. 328, No. 1, 9-16; Y. Shimizu, A. Inoue, Y.

Tomari, T. Suzuki, T. Yokogawa, K. Nishikawa and T. Ueda (2001) "Cell-free translation reconstituted with purified components" Nature Biotechnology Vol. 19, No. 8, 751-755; H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276). The reconstituted cell-free translation systems are freed of elements irrelevant to translation by fractionating a cell-free translation system based on an *E. coli* extract and reassembling fractions so that inclusion of inhibitors such as nucleases and proteases can be prevented more easily than in conventional cell-free translation systems using cell extracts. Transcription from DNA and translation can also be simultaneously performed by adding elements necessary for transcription reaction.

If such a cell-free coupled transcription-translation system is used, mRNA synthesis by transcription from template DNA can take place in the same system as translation reaction. Moreover, if complex formation between an mRNA and a linker molecule could also take place in the same system, transcription of cDNA to preparation of an mRNA-peptide fusion could be accomplished in one pot (in the same reaction vessel), unlike conventional mRNA display methods. The first object of the present invention is to provide a display method taking advantage of such a reconstituted cell-free translation system capable of controlling components of the reaction system.

Further, the second object of the present invention is to make it possible to construct an mRNA or cDNA library presenting unusual peptides by combining such a display method with a previously reported technique for synthesizing a unusual peptide using a ribozyme capable of catalyzing the synthesis of an acylated tRNA (flexizyme).

Solution to Problems

The RAPID display method of the present invention made it possible to completely accomplish transcription, translation and linker-mRNA complex formation followed by linkage between the peptide and the linker in a single translation system by modifying mRNA display to replace the puromycin-conjugated linker by a linker molecule now developed by us and further optimizing the reconstituted cell-free translation system.

As compared with conventional mRNA display methods, the RAPID display method mainly has the following features.

(a) The 3' end of the linker molecule has a structure in which an amino acid is attached to adenosine via an ester (i.e., aminoacylated) rather than puromycin.
(b) Aminoacylation reaction is mediated by an artificial RNA catalyst (ribozyme).
(c) A reconstituted cell-free translation system is used.
(d) The fusion between the linker and an mRNA is made by complex formation based on hybridization in a translation system rather than ligation.
(e) Transcription, translation and complex formation with the linker can be performed in a single translation reaction vessel.

Moreover, unusual peptides can also be presented as phenotypes by applying techniques for synthesizing unusual peptides by translation in the same translation system. Acylation reaction for charging a tRNA with a non-proteinogenic amino acid or hydroxy acid, which is a constituent unit of a unusual peptide, is also mediated by an artificial RNA catalyst (ribozyme).

The present invention is summarized as follows.

(1) A linker used for preparing a conjugate in which an mRNA and a peptide as a translation product thereof are coupled via the linker in a reconstituted in vitro protein synthesis system, said linker comprising:
a single-stranded structure region having side chain bases pairing with the bases at the 3'-end of the mRNA at one end of the linker, and
a peptidyl acceptor region having a group capable of binding to the translation product by peptidyl transfer reaction at the other end of the linker,
wherein the peptidyl acceptor region has a structure containing an amino acid attached to an oligo RNA consisting of a nucleotide sequence of ACCA via an ester bond; and said ester bond is formed by an aminoacylation reaction using an artificial RNA catalyst.
(2) The linker as defined in (1) above wherein the single-stranded structure region and the peptidyl acceptor region are connected via a polyethylene glycol moiety.
(3) The linker as defined in (1) or (2) above wherein the single-stranded structure region consists of a single-stranded DNA.
(4) The linker as defined in any one of (1)-(3) above wherein the artificial RNA catalyst used in the aminoacylation reaction has a chemical structure consisting of any one of the RNA sequences below:

```
                                               (SEQ ID NO: 3)
GGAUCGAAAGAUUUCCGCAGGCCCGAAAGGGUAUUGGCGUUAGGU (SEQ ID NO: 4)
GGAUCGAAAGAUUUCCGCGGCCCCGAAAGGGAUUAGCGUUAGGU (SEQ ID NO: 5)
GGAUCGAAAGAUUUCCGCAUCCCCGAAAGGGUACAUGGCGUUAGGU (SEQ ID NO: 19)
GGAUCGAAAGAUUUCCGCACCCCCGAAAGGGUAAGUGGCGUUAGGU.
```

(5) A process for preparing an [mRNA]-[linker]-[peptide] conjugate in which an mRNA and a peptide as a translation product thereof are coupled via the linker as defined in any one of (1)-(4) above, said process comprising the steps of:
preparing the linker as defined in any one of (1)-(4) above;
synthesizing an mRNA having a sequence capable of hybridizing with the base sequence of the single-stranded structure region of the linker downstream of a sequence encoding a peptide; and
contacting the linker with the mRNA and translating the mRNA into the peptide in a reconstituted in vitro protein synthesis reaction solution.
(6) A process for preparing an [mRNA]-[linker]-[peptide] conjugate in which an mRNA and a peptide as a translation product thereof are coupled via the linker as defined in any one of (1)-(4) above, said process comprising the steps of:
preparing the linker as defined in any one of (1)-(4) above,
synthesizing a template DNA for an mRNA having a sequence capable of hybridizing with the base sequence of the single-stranded structure region of the linker downstream of a sequence encoding a peptide, and
introducing the linker and the DNA into a reconstituted in vitro protein synthesis reaction solution, thereby performing transcription from the DNA into the mRNA and translation into the peptide as well as complex formation between the linker and the mRNA.

(7) The process as defined in (5) or (6) above wherein the reconstituted in vitro protein synthesis reaction solution contains a tRNA charged with a non-proteinogenic amino acid or hydroxy acid, whereby the translated peptide constitutes a unusual peptide.

(8) A library comprising [mRNA]-[linker]-[unusual peptide] conjugates prepared by the process as defined in (7) above.

(9) A method for selecting a peptide aptamer that binds to a target substance from a library of [mRNA]-[linker]-[peptide] conjugates in which each mRNA and a peptide as a translation product thereof are coupled via the linker as defined in any one of (1)-(4) above, said method comprising the steps of:

preparing the linker as defined in any one of (1)-(4) above;
preparing an mRNA library comprising mRNAs each having a sequence capable of hybridizing with the base sequence of the single-stranded structure region of the linker downstream of a sequence encoding a random peptide sequence;
contacting the linker with the mRNA library and performing translation into the peptide in a reconstituted in vitro protein synthesis reaction solution, thereby preparing an [mRNA]-[linker]-[peptide] conjugate library;
contacting the target substance with the [mRNA]-[linker]-[peptide] conjugate library; and selecting a conjugate presenting the peptide bound to the target substance.

(10) The method as defined in (9) above wherein the target substance has been biotinylated.

(11) The method as defined in (9) or (10) above wherein the reconstituted in vitro protein synthesis reaction solution contains a tRNA charged with a non-proteinogenic amino acid or hydroxy acid, whereby the translated peptide constitutes a unusual peptide.

(12) A process for preparing the linker as defined in (2) above, said process comprising the steps of:

synthesizing a chimeric oligonucleotide consisting of the single-stranded structure region and an oligo RNA of a sequence of ACCA connected via a polyethylene glycol moiety; and attaching an amino acid to adenosine at the 3' end of the chimeric oligonucleotide via an ester bond by a reaction using an artificial RNA catalyst,
thereby preparing a linker consisting of the single-stranded structure region and the peptidyl acceptor region connected via the polyethylene glycol moiety.

(13) The process as defined in (12) above wherein the artificial RNA catalyst has a chemical structure consisting of any one of the RNA sequences below:

```
                                              (SEQ ID NO: 3)
GGAUCGAAAGAUUUCCGCAGGCCCGAAAGGGUAUUGGCGUUAGGU (SEQ ID NO: 4)
GGAUCGAAAGAUUUCCGCGGCCCCGAAAGGGGAUUAGCGUUAGGU (SEQ ID NO: 5)
GGAUCGAAAGAUUUCCGCAUCCCCGAAAGGGUACAUGGCGUUAGGU (SEQ ID NO: 19)
GGAUCGAAAGAUUUCCGCACCCCCGAAAGGGGUAAGUGGCGUUAGGU.
```

Advantageous Effects of Invention

By using a linker molecule capable of binding to an mRNA in a reconstituted cell-free translation reaction solution, an [mRNA]-[linker]-[peptide] conjugate can be prepared only by adding the linker and a cDNA or mRNA to perform translation reaction in a single reaction vessel.

Moreover, an [mRNA]-[linker]-[unusual peptide] conjugate presenting a unusual peptide synthesized by translation from sequence information of a template nucleic acid molecule can be obtained by introducing a tRNA charged with a non-proteinogenic amino acid or hydroxy acid into the same reconstituted cell-free translation reaction solution.

Thus, a gene library of artificial peptide aptamers expected to improve in vivo stability and binding affinity for a target protein can be simply constructed by combining the RAPID display method with a technique for synthesizing a unusual peptide by translation.

DETAILED DESCRIPTION OF THE INVENTION

1. Linker

The linker in the RAPID display method of the present invention connects an mRNA and a peptide translated therefrom by binding to the 3' end of the mRNA at one end and to the C-terminus of the peptide at the other end in the same manner as in known mRNA display methods.

However, the linker in the RAPID display method of the present invention differs in the structure of both ends from those used in known mRNA display methods. The linker used in the RAPID display method of the present invention is herein sometimes referred to as "RAPID linker".

First, the region at one end of the linker binding to the C-terminus of a peptide is explained. This region is herein sometimes referred to as "peptidyl acceptor" or simply "acceptor". Thus, the term "peptidyl acceptor" refers to a molecule having a structure capable of binding to a peptide growing by peptidyl transfer reaction on a ribosome (peptidyl-tRNA). The peptidyl acceptor may refer to a region located at an end of a linker or may refer to a whole structure including a linker. For example, the peptidyl acceptor in known mRNA display methods is puromycin located at one end of a linker or a puromycin-conjugated linker as a whole structure including a linker.

The RAPID linker of the present invention is characterized by the structure and the preparation process of the peptidyl acceptor.

In the RAPID display method, a linker having a sequence consisting of a 4-residue ribonucleotide ACCA is synthesized at the 3' end, and then a given amino acid is attached to adenosine at the 3' end, thereby conferring a structure as peptidyl acceptor on the linker. During peptide elongation reaction on a ribosome, the amino acid attached to the end of the linker accepts the C-terminus of the peptide of the peptidyl-tRNA and binds to the peptide. The structure in which an amino acid is attached to the RNA sequence ACCA via an ester bond is herein referred to as "peptidyl acceptor region".

Figure 1A:
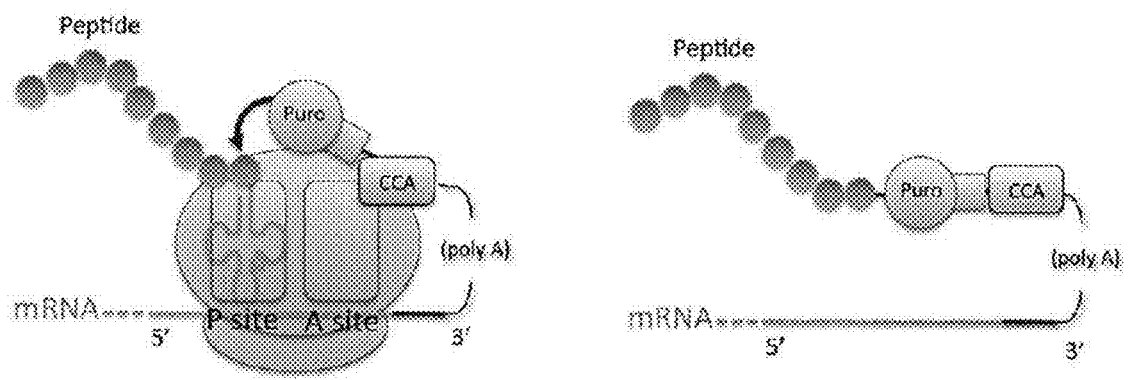
FIG. 1A schematically shows the process in which a translated peptide molecule is coupled to an mRNA via a puromycin-conjugated linker in mRNA display.
Figure 1B:
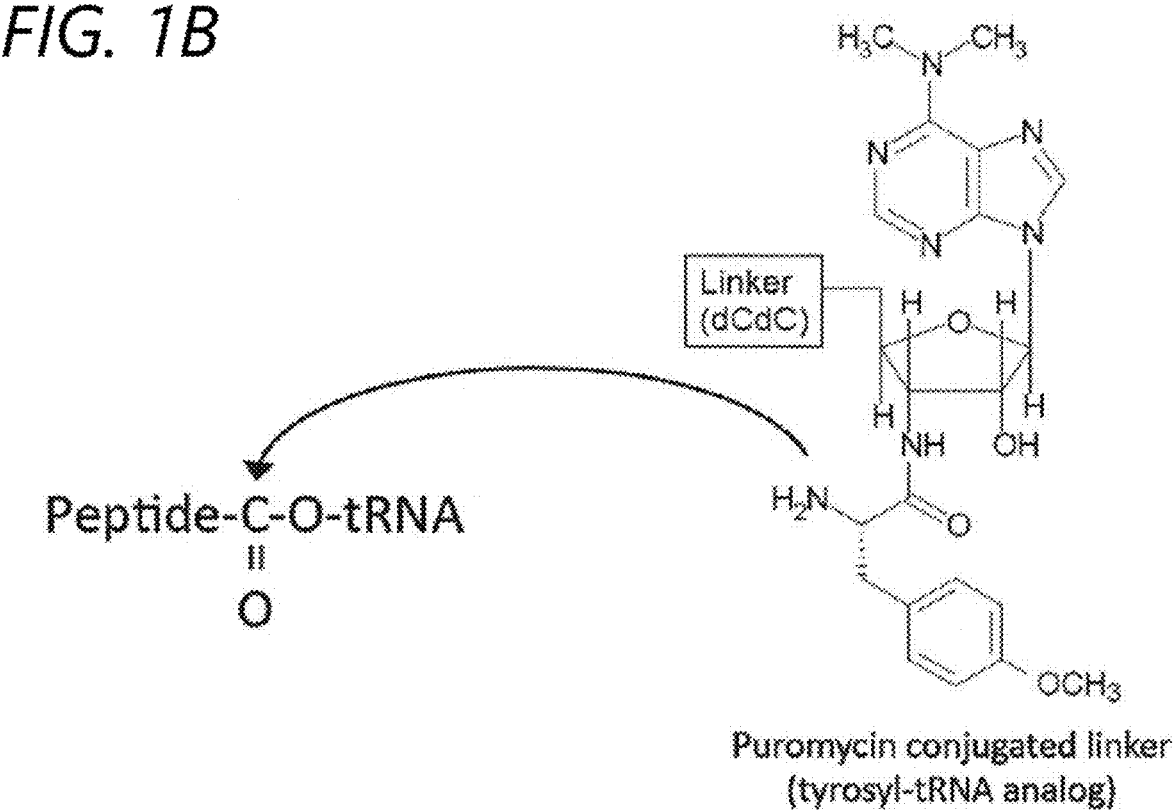
FIG. 1B shows the structure of the peptidyl acceptor region of the linker (puromycin-conjugated linker).

The peptidyl acceptor in known mRNA display methods is puromycin that has an aminonucleoside structure in which a ribose in the adenosine-like moiety and an amino acid are linked via an amide bond. In the RAPID display method of the present invention, however, an amino acid is attached to the 3'-O of ribose via an ester bond. In other words, the peptidyl acceptor in the RAPID display of the present invention has a nucleoside structure similar to that of natural aminoacyl-tRNA. See FIG. 2B showing the structure of a linker to which L-phenylalanine is attached as an example of such a peptidyl acceptor (L-Phe-conjugated linker) in comparison with FIG. 1B (puromycin-conjugated linker). In the present invention, the peptidyl acceptor shows an incorporation efficiency comparable to or higher than that of puromycin by adopting a structure closer to that of the natural acceptor.

The formation of a bond between the peptidyl acceptor and the C-terminus of the peptide seems to occur by the proximity of the amino group of the peptidyl acceptor incorporated into the A site to the ester bond at the C-terminus of the attached peptide of the peptidyl-tRNA in the P site in the same manner as normal peptidyl transfer reaction in ribosomes. Thus, the covalent bond formed with the C-terminus of the peptide chain is typically an amide bond in the same manner as in mRNA display. It should be noted that a linker having an unnatural (non-proteinogenic) amino acid such as a D-amino acid or β (beta)-amino acid can also be used in the RAPID display of the present invention by using an artificial RNA catalyst (flexizyme) for the synthesis of the linker.

Next, binding to an mRNA at the other end of the linker is explained.

In the RAPID display method of the present invention, the 5' end of the linker and the 3' end of a mRNA molecule forms a complex by hybridization based on base pairing. Thus, the 5' end of the linker assumes a single-stranded structure having a nucleic acid base in the side chain. This region in the RAPID linker is herein referred to as "single-stranded structure region". Specific examples of single-stranded structures having a nucleic acid base in the side chain include single-stranded DNAs, single-stranded RNAs, single-stranded PNAs (peptide nucleic acids), etc. The resulting complexes must be also stably kept during peptide selection. As the complementarity between the nucleotide sequence of the single-stranded structure region of the linker and the sequence of the 3' end of the mRNA molecule increases, the efficiency of double-strand formation increases and stability also increases. Stability also depends on the GC content, the salt concentration of the reaction solution, and reaction temperature. Especially, this region desirably has a high GC content, specifically a GC content of 80% or more, preferably 85% or more. Specific examples of such structures at the 5' end of the linker include, but in any way are not limited to, single-stranded DNAs consisting of 13-21 nucleotides used in the Examples herein below having the nucleotide sequences:

(SEQ ID NO: 1)
5'-CTCCCGCCCCCCGTCC-3'

(SEQ ID NO: 2)
5'-CCCGCCTCCCGCCCCCCGTCC-3'.

The rest of the linker excluding both ends is designed to have a flexible, hydrophilic and simple linear structure with less side chains as a whole similarly to the structure of linkers used in known mRNA display methods. Therefore, linear polymers including, for example, oligonucleotides such as single- or double-stranded DNA or RNA; polyalkylenes such as polyethylene; polyalkylene glycols such as polyethylene glycol; polystyrenes; polysaccharides; or combinations thereof can be appropriately selected and used. The linker preferably has a length of 100 angstroms or more, more preferably about 100-1000 angstroms.

A specific non-limiting example of linkers that can be used in the present invention includes a chimeric DNA/RNA oligonucleotide comprising a single-stranded structure region consisting of a single-stranded DNA having a high-GC content sequence and an RNA consisting of an ACCA sequence at the 3' end wherein the DNA and RNA are connected via a polyethylene glycol moiety (PEG linker). For example, a typical example includes [DNA]-[Spacer-18]$_n$-rArCrCrA (wherein Spacer18 is hexaethylene glycol, and n is an integer of 4-8) synthesized in Example 1.

2. Amino Acid Modification of the Linker

As indicated above, it is necessary to attach an amino acid to the oligo RNA moiety (ACCA sequence) at an end of the linker molecule in order to confer a structure as a peptidyl acceptor on the linker. The present invention is characterized in that this attachment of an amino acid takes place using an artificial RNA catalyst.

It is theoretically possible to attach an amino acid to the 3'-O of an oligo RNA synthesized by conventional chemical synthesis such as solid-phase synthesis via an ester, but it is practically impossible to introduce the synthetic product into a cell-free translation system after post-treatment of synthesis reaction because it is highly reactive and lacks stability. In the present invention, this problem is solved by aminoacylation reaction of the oligo RNA using a "flexizyme", which is an artificial RNA catalyst developed as an aminoacyl-tRNA synthetase. In this method, aminoacylation reaction can be performed under mild conditions and the product can be introduced into a translation system and used in it only after simple post-treatment. For details, see the following documents:

H. Murakami, H. Saito, and H. Suga, (2003), Chemistry & Biology, Vol. 10, 655-662;

H. Murakami, D. Kourouklis, and H. Suga, (2003), Chemistry & Biology, Vol. 10, 1077-1084;

H. Murakami, A. Ohta, H. Ashigai, H. Suga (2006) Nature Methods 3, 357-359;

N. Niwa, Y. Yamagishi, H. Murakami, H. Suga (2009) Bioorganic & Medicinal Chemistry Letters 19, 3892-3894; and JPA-2008-125396 or WO2007/066627.

Flexizymes are also known by designations such as dinitrobenzyl flexizyme (dFx), enhanced flexizyme (eFx), amino flexizyme (aFx), etc. Flexizymes have the ability to catalyze aminoacylation of adenosine at the 3' end using a weakly activated amino acid as a substrate by recognizing the carbonyl group with which the amino acid reacts, an aromatic ring in the side chain or leaving group of the amino acid, and an ACC-3' sequence at the 3' end of the linker. This is why an oligo RNA structure consisting of an ACCA-3' sequence is essential at the end of the RAPID linker. Flexizyme-mediated aminoacylation reaction proceeds only by placing an amino acid substrate and a linker molecule having a cognate oligo RNA moiety on ice in the presence of a flexizyme for about 2 hours.

In the present invention, flexizymes having the sequences shown below are suitably used.

Original Flexizyme Fx

```
Original flexizyme Fx
                                    (SEQ ID NO: 3)
[GGAUCGAAAGAUUUCCGCAGGCCCGAAAGGGUAUUGGCGUUAG GU-3', 45nt]

Enhanced flexizyme eFx
                                    (SEQ ID NO: 4)
[5'-GGAUCGAAAGAUUUCCGCGGCCCCGAAAGGGGAUUAGCGU UAGGU-3', 45nt])

Dinitrobenzyl flexizyme dFx
                                    (SEQ ID NO: 5)
[5'-GGAUCGAAAGAUUUCCGCAUCCCCGAAAGGGUACAUGGCG UUAGGU-3', 46nt]

Amino flexizyme aFx
                                    (SEQ ID NO: 19)
[5'-GGAUCGAAAGAUUUCCGCACCCCCGAAAGGGGUAAGUGGC GUUAGGU-3', 47nt])
```

Flexizyme Fx is capable of catalyzing aminoacylation using amino acid substrates having a cyanomethyl leaving group and a side chain aromatic ring (e.g., cyanomethyl esters of phenylalanine, tyrosine, etc.), while flexizymes eFx, dFx, aFx are capable of catalyzing aminoacylation using amino acid substrates having a 4-chlorobenzylthiol leaving group and a non-aromatic ring side chain in addition to the leaving groups and side chains that can be used with flexizyme Fx. For details, see the documents cited above. By reacting an amino acid having such a structure and a linker in the presence of a flexizyme, therefore, a molecule in which the amino acid is attached via an ester bond to the 3'-hydroxyl group on the ribose ring in adenosine at the 3' end of the linker can be obtained. Amino acid substrates having any structure can be attached, including not only amino acids used in natural translation but also non-proteinogenic amino acids such as D-amino acids or R (beta)-amino acids (i.e., other than L-amino acids normally found in naturally occurring proteins). Further, a hydroxycarboxylic acid instead of an amino acid can be attached to the 3' end of the linker or incorporated as a peptidyl acceptor into a ribosome.

3. Reaction in a Translation System

According to the RAPID display method, a linker is added to a cell-free translation system (also referred to as "in vitro protein synthesis system") along with a cDNA or mRNA and reacted for a predetermined period, thereby allowing for translation from the mRNA and complex formation with the linker molecule followed by linkage between the peptide and the linker.

The cell-free translation system used can be a conventional reconstituted cell-free translation systems with appropriate modifications, and transcription from DNA can also be performed in the same system as used for translation if it contains a DNA-dependent RNA polymerase (preferably T7RNA polymerase).

The following reactions (a) to (d) can be performed in a single reaction vessel (one-pot), if it is a coupled transcription-translation synthesis system:
(a) a reaction in which a DNA is transcribed into an mRNA;
(b) a reaction in which the 3' end of the mRNA forms a complex with the single-stranded structure region at an end of a linker via hybridization;
(c) a reaction in which the mRNA is translated into a peptide;
(d) a reaction in which the C-terminus of the translated peptide binds to the peptidyl acceptor region at the other end of the linker via an amide bond;
(e) a reaction in which a [peptide]-[linker]-[mRNA] complex is released from the ribosome.

Alternatively, a series of reactions starting from (b) are performed in a reconstituted cell-free translation system, when a preliminarily prepared mRNA is added to the translation system along with a linker.

A reconstituted cell-free translation system should comprise purified ribosomes, translation initiation factors, translation elongation factors, an mRNA, an aminoacyl-tRNA, ATP or GTP used as a substrate, etc. (M. H. Schreier, B. Erni and T. Staehelin (1977) "Initiation of mammalian protein synthesis. I. Purification and characterization of seven initiation factors." Journal of Molecular Biology, Vol. 116, No. 4, 727-53. H. Trachsel, B. Erni, M. H. Schreier and T. Staehelin (1977) "Initiation of mammalian protein synthesis. II. The assembly of the initiation complex with purified initiation factors." Journal of Molecular Biology, Vol. 116, No. 4, 755-67). Among them, the aminoacyl-tRNA can be replaced by adding a tRNA, an aminoacyl-tRNA synthetase and its substrate into the same reaction solution. Additionally, proteins or enzymes and their substrates such as translation termination factors, ribosome recycling factors, creatine kinase, myokinase, nucleotide diphosphate kinase, pyrophosphatase can be added to increase the efficiency or fidelity of translation reaction as common in conventional cell-free translation systems (P. C. Jelenc and C. G. Kurland (1979) "Nucleoside triphosphate regeneration decreases the frequency of translation errors" Proceedings of the Natural Academy Science of the United States of America Vol. 76, No. 7, 3174-3178). When transcription reaction is to be performed simultaneously with translation, a cDNA as well as T7 RNA polymerase and its substrate can be added in place of mRNA.

In the present invention, a DNA or RNA having a necessary sequence is introduced into a cell-free translation system comprising components optimized for an intended purpose. The sequence of the DNA or RNA should be such that a cDNA is transcribed into an mRNA and that translation of the mRNA starts in the synthesis system used. The full length of the region encoding the amino acid sequence of a peptide should be translated to the end, and a spacer sequence consisting of a peptide for conferring flexibility is also fused to the C-terminus of the translated amino acid, immediately followed by a stop codon. For example, a peptide sequence (Cys-(Gly-Ser-)x3) and an amber codon (stop codon) immediately downstream of it are encoded. Additionally, the 3' end of the mRNA has a structure capable of hybridizing with the single-stranded structure region of a linker to form a double strand, so that the downstream of the coding region (immediately downstream of the stop codon) should have a sequence complementary to the sequence of the single-stranded structure region. The sequence of this region (double strand-forming region) is herein referred to as linker hybridization sequence.

Specifically, the cDNA or mRNA desirably contains the following sequences:

(1) A promoter sequence compatible with the RNA polymerase used in the cDNA. TAATACGACTCACTATA (SEQ ID NO: 6) in the case of T7 promoter.

(2) A sequence encoding a relevant sequence upstream of a start codon.

When *E. coli*-derived ribosomes are used in a cell-free translation system, the gene for the SD sequence is included. This is also found in conventional protein synthesis. For example, GGGTTAACTTTAA GAAGGAGATATACAT (SEQ ID NO: 7): a modified sequence upstream of gene 10 protein of T7 phage. The SD sequence is underlined.

(3) A sequence constituting an ORF [a sequence encoding an amino acid sequence having a spacer fused to the C-terminus of a peptide aptamer] of a variant gene library, beginning with a start codon (ATG).

Depending on the stop codon used here, its cognate release factor should be removed from the cell-free translation system. A cell-free translation reaction solution is prepared by removing RF1 when TAG (amber codon) is used, or removing RF2 when TGA (opal codon) is used, or removing both RF1 and RF2 when TAA (ochre codon) is used.

(4) A sequence encoding a double strand-forming region (linker hybridization sequence).

The reconstituted cell-free translation reaction solution used in the present invention preferably contains components adapted for intended purposes. For example, the release factor cognate to the amber codon, a peptidyl-tRNA hydrolase (PTH), which is an enzyme cleaving peptidyl-tRNA, and the like are removed in the Examples herein below.

Further, an acylated tRNA preliminarily charged with a desired non-proteinogenic amino acid (or hydroxy acid) (i.e., having an activated amino acid attached thereto) can be added to a reconstituted cell-free translation system containing only limited natural amino acids. By correlating the codons for excluded natural amino acids with the anticodon of the tRNA acylated with a non-proteinogenic amino acid (or hydroxy acid), a peptide containing the non-proteinogenic amino acid (or hydroxy acid) can be synthesized by translation on a ribosome on the basis of genetic information of the mRNA. Alternatively, a unusual peptide containing no natural amino acid can also be synthesized by translation by adding an acylated tRNA charged with a non-proteinogenic amino acid (or hydroxy acid) to a reconstituted cell-free translation system containing no natural amino acid.

Acylated tRNAs charged with a non-proteinogenic amino acid (or hydroxy acid) can be prepared by using the artificial RNA catalysts "flexizymes" capable of catalyzing aminoacyl-tRNA synthesis as described above. As indicated above, these artificial RNA catalysts are capable of charging an amino acid having any side chain and also have the function of recognizing only a consensus sequence 5'-RCC-3' (R=A or G) at the 3' end of tRNAs to acylate the 3' end of the tRNAs, and therefore, they can act on any tRNAs having different anticodons. Moreover, the recognition site in an amino acid contains no substituent at the α position, so that not only L-amino acids but also hydroxy acids (having a hydroxyl group at the α-position), N-methylamino acids (having an N-methylamino acid at the α-position), N-acylamino acids (having an N-acylamino group at the α-position), D-amino acids and the like can be used as substrates. Detailed description can be found in the documents about flexizymes cited above as well as in Y. Goto, H. Suga (2009) "Translation initiation with initiator tRNA charged with exotic peptides" Journal of the American Chemical Society, Vol. 131, No. 14, 5040-5041, WO2008/059823 entitled by "TRANSLATION AND SYNTHESIS OF POLYPEPTIDE HAVING NONNATIVE STRUCTURE AT N-TERMINUS AND APPLICATION THEREOF", Goto et al., ACS Chem. Biol., 2008, 3, 120-129, WO2008/117833 entitled by "PROCESS FOR SYNTHESIZING CYCLIC PEPTIDE COMPOUND", etc.

A comprehensive technology for translation/synthesis, modification and screening of peptides based on a core technology consisting of a synthesis system of unusual peptides (a concept including both kit and synthesis method) using a tRNA acylated with a non-proteinogenic amino acid or hydroxy acid via a "flexizyme" was designated by us as RAPID system (Random Peptide Integrated Discovery system). The RAPID system allows for the translation/synthesis of various unusual peptides as in vitro translation products based on template mRNAs of relevant sequences. It should be understood from the foregoing description that unusual peptides as used herein refer to polymers containing the various substrates described above as their components and include any translation products that can be synthesized by the RAPID system other than twenty natural amino acids, including amino acids having various side chains, β (beta)-amino acids, γ (gamma)-amino acids and δ (delta)-amino acids, D-amino acids, and derivatives having a structure in which an amino group or a carboxyl group on the amino acid backbone is substituted. Further, unusual peptides may have a backbone structure other than normal amide bonds. For example, unusual peptides also include depsipeptides consisting of amino and hydroxy acids, polyesters produced by continuous condensation of hydroxy acids, peptides methylated at the nitrogen atom of the amide bond by introducing an N-methylamino acid, and peptides having various acyl groups (acetyl, pyroglutamic acid, fatty acids, etc.) at the N-terminus. Furthermore, cyclic peptides obtained by circularizing non-cyclic peptides consisting of an amino acid sequence bearing a pair of functional groups capable of forming a bond between them at opposite ends can also be synthesized by the RAPID system (or cyclic N-methylpeptides can be obtained if N-methylpeptides are used). Circularization may occur under the conditions of cell-free translation systems with a pair of some functional groups, as exemplified by a cyclic peptide circularized via a thioether bond obtained by translation/synthesis of a peptide sequence bearing a chloroacetyl group and a cysteine group at opposite ends as shown in the Examples herein below.

The RAPID system allows for the synthesis of peptides having various structures only by changing template mRNAs because unusual peptides are synthesized by ribosomal translation. If translation/synthesis is performed using an mRNA (or corresponding DNA) containing a random sequence, a random peptide library can be readily constructed. The RAPID display method of the present invention is suitably used to link unusual peptides synthesized by the RAPID system to mRNAs representing their genotypes. The RAPID linker of the present invention is added along with a template cDNA or mRNA to a cell-free translation system optimized for the synthesis of a unusual peptide and the mixture is reacted for a predetermined period, whereby the unusual peptide as the resulting translation product is coupled to the mRNA via the linker and presented.

Next, the linkage between the linker and the mRNA occurring in the cell-free translation system is explained. As described in the section of Background Art, it was necessary to ligate the linker and the mRNA outside the translation system at a stage prior to translation reaction in known mRNA display methods. In contrast, the RAPID display method of the present invention is characterized in that complex formation between the linker and the mRNA by hybridization can be carried out in the translation system.

Figure 2A:
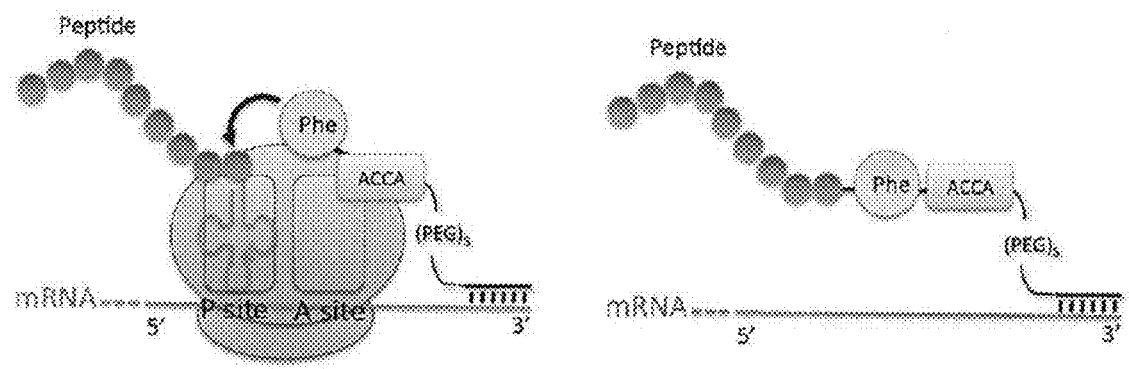
FIG. 2A schematically shows the process in which a translated peptide molecule is coupled to an mRNA via an RAPID linker (e.g., an L-Phe-conjugated linker shown as an example) in the RAPID display method of the present invention.
Figure 2B:
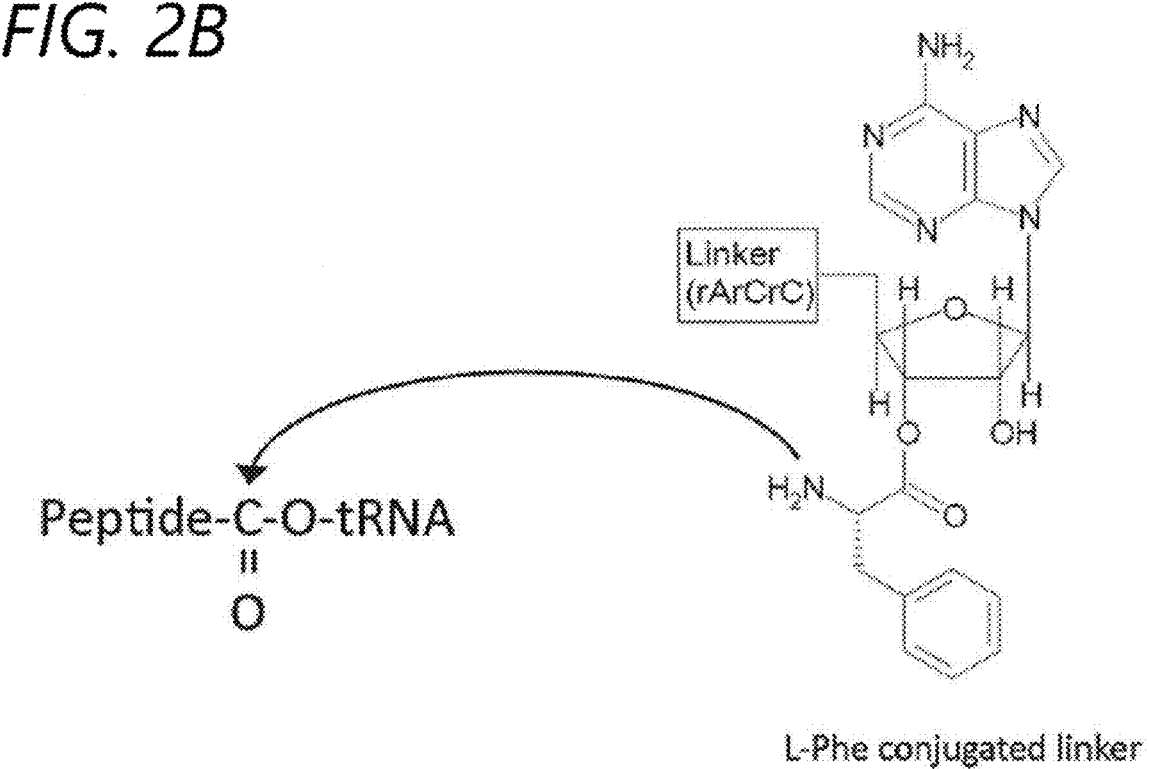
FIG. 2B shows the structure of the peptidyl acceptor region of the linker (L-Phe-conjugated linker).

With reference to FIG. 2, the process in which hybridization between an mRNA and a RAPID linker, synthesis of a peptide molecule and fusion of the linker to the C-terminus of the peptide take place by introducing the mRNA along with the linker into a cell-free translation system is explained.

As indicated above, the linkage between the mRNA and the linker results from the formation of a double strand via a hydrogen bond between the base sequence of the single-stranded structure region of the linker and a complementary base sequence at the 3' end of the mRNA. This linkage is made to map the mRNA to the translated peptide molecule, so that an [mRNA]-[linker]-[peptide] complex formed during translation on a ribosome must be also stably kept during the selection of the translated peptide.

By introducing an mRNA along with an RAPID linker into a cell-free translation system, a ribosome is located on the mRNA and translation reaction starts, whereby a peptide chain elongates and the terminated peptide chain binds to the amino acid of a peptidyl acceptor region consisting of [rACCA-amino acid] of the linker at the C-terminus and dissociates from tRNA. Without wishing to limit the concept of the present invention but for illustrative purposes only, we believe that the hybridization between the mRNA and the RAPID linker may occur at a stage before the elongation reaction of a peptide chain starts if the mRNA and the RAPID linker are introduced into the cell-free translation system at the same time. Alternatively, complex formation by hybridization between the mRNA and the RAPID linker on the ribosome properly occurs even when transcription from a cDNA and translation reaction take place first and then the linker is added into the translation reaction solution lacking termination factors and PTH. Then, a covalent linkage seems to occur between [rACCA-amino acid] at an end of the linker and the C-terminus of the peptide when this moiety accidentally enters the ribosomal A site at the end of translation. The reaction occurs with high efficiency because hybridization between the mRNA and the linker has already occurred at the end of translation and this [rACCA-amino acid] substrate is connected to the mRNA on the ribosome via the linker and shows a locally very high concentration.

The fact that the [mRNA]-[linker]-[peptide] complex thus formed on the ribosome is stably kept even after the peptide chain dissociates from the ribosome is also supported in the Examples herein below.

4. Selection of a Peptide Aptamer

In evolutionary molecular engineering, large amounts of potential genes are provided and clones having a target phenotype are selected from them in order to create a protein or peptide having a desired function or property.

Basically, a DNA population is prepared first to give an RNA population as an in vitro transcript, and then a peptide population as an in vitro translation product. From this peptide population, a peptide having a desired function or property is selected by some screening system. If one wishes to obtain a peptide molecule binding to a specific protein, for example, the peptide population is injected into a target protein-immobilized column, whereby a mixture of peptide molecules bound to the column can be recovered. The template mRNA fused to each peptide molecule like a tag in a population of the recovered peptide-mRNA complexes is converted back into the DNA by reverse transcriptase to give a biased library containing a lot of clones having a target phenotype amplified by PCR, and then similar selection experiments are performed again. Alternatively, it is also possible to perform reverse transcription reaction before selection for the purpose of making nucleic acid moieties double-stranded in order to avoid the possibility of recovering an RNA aptamer. By repeating this procedure, clones having a desired phenotype become concentrated in the population over generations.

To identify a peptide aptamer, the gene for a peptide aptamer binding to a target substance can be cloned by repeating the steps of mixing a library of mapped molecules and the target substance, selecting mapped molecules presenting peptides bound to the target substance (active species), and preparing a nucleic acid library by PCR from nucleic acid moieties of the mapped molecules selected. The step of selecting mapped molecules bound to the target substance can be accomplished by allowing [RNA (or DNA/RNA hybrid)]-[linker]-[peptide] complexes to bind to the target substance and separating them from other complexes by an appropriate method to identify a peptide having a desired binding property.

The target substance may be a protein, nucleic acid, carbohydrate, lipid or any other compound. It is convenient to derivatize the target substance with a label isolatable by binding to a solid phase in order to separate active species complexes binding to the target substance from other complexes. For example, the target substance is biotinylated and isolated by specific binding to an immobilized biotin-binding protein in the Examples herein below. Such specific binding pairs that can be used include, but are not limited to, biotin-binding protein (avidin, streptavidin, etc.)/biotin pairs as well as maltose-binding protein/maltose, polyhistidine peptide/metal ion (nickel, cobalt, etc.), glutathione-S-transferase/glutathione, antibody/antigen (epitope), etc.

By using evolutionary molecular engineering, it is possible in principle to obtain a peptide having a non-naturally occurring amino acid sequence from a gene library of DNA sequences consisting of randomly connected four bases A, T, G, C. Further, a unusual peptide containing a non-proteinogenic amino acid (or hydroxy acid) can also be synthesized by translation as an in vitro translation product by introducing a tRNA acylated with the non-proteinogenic amino acid (or hydroxy acid) into a translation system. A library of unusual peptides can be efficiently obtained by repeating the steps of selecting an active species presenting a peptide having a desired binding property from a population of complexes of a unusual peptide and an mRNA (or cDNA), amplifying a mapped gene moiety and translating it again.

For details of molecular biology techniques with respect to the description herein above and below in the Examples, see, for example, Sambrook, Molecular Cloning: A Laboratory Manual, 3rd edition, Cold Spring Harbor Laboratory Press, 2001; Golemis, Protein-Protein Interactions: A Molecular Cloning Manual, 2nd edition, Cold Spring Laboratory Press, 2005, etc.

The following examples further illustrate the present invention. However, these examples are only for illustrating the present invention but should not be construed to limit the scope of the present invention.

Example 1

[Synthesis of Linkers]

Chimeric DNA/RNA oligonucleotides comprising a DNA and a RNA connected via polyethylene glycol (5 units of Spacer18) were used as linkers. Various linkers were purchased from BEX (Tokyo). In the sequence shown below, *A and *C correspond to RNA, and SPC18 corresponds to Spacer18 (hexaethylene glycol).

an21-ACA:
5'-CCCGCCTCCCGCCCCCCGTCC-[SPC18]$_5$-A*-C*-C*-A*-3'

[Aminoacylation of the Linkers]

L-phenylalanine or β-L-alanine was attached to the 3' end of the an21-ACCA linker molecule via an ester bond by a flexizyme-catalyzed reaction. The reaction product was identified by acrylamide electrophoretic analysis of the purified reaction product solution under acidic conditions. If the bands derived from the linker molecule are aminoacylated, the mobility decreases. Thus, aminoacylation efficiency can be determined by comparing the intensity of bands derived from unreacted materials and bands derived from the reaction product.

Acylation reaction for attaching L-phenylalanine was performed by adding 5 μL of 20 μM flexizyme eFx, 20 μM an21-ACCA linker, and a substrate (L-phenylalanine cyanomethyl ester) to 20% dimethyl sulfoxide in 0.1 M HEPES-potassium buffer (pH 7.5), 600 mM magnesium chloride, and reacting the mixture on ice for 2 hours. Specifically, 40 μM linker molecule dissolved in pure water and flexizyme eFx (200 μM, 0.5 μL) were first added to 0.2 M HEPES-potassium buffer (pH 7.5), and the mixture was heated on a thermoblock (ND-MD1, Nissin Scientific Corporation) at 95° C. for 2 minutes, and allowed to stand at room temperature for 5 minutes. Then, acylation reaction of the linker molecule was started by adding magnesium chloride (3 M, 1 μL) and a substrate (25 mM in dimethyl sulfoxide, 1 μL) on ice, and the mixture was allowed to stand on ice for 2 hours. For attaching β-L-alanine, β-L-alanine p-chlorobenzyl thioether was used as a substrate under the same conditions at pH 8.0. The reaction was quenched by adding 40 μL of 0.3 M sodium acetate (pH 5.0). The reaction product was precipitated with ethanol, and the pellet was washed with 70% ethanol and dissolved in 10 μL of 1 mM sodium acetate. After the reaction, the solution was separated by 20% denaturing polyacrylamide gel electrophoresis (50 mM sodium acetate (pH 5.0), 6 M urea) under acidic conditions, and the gel after migration was analyzed by fluorescent staining with SYBR Green II (Invitrogen, SYBR is a registered trademark of Molecular Probes Inc.).

Figure 3:
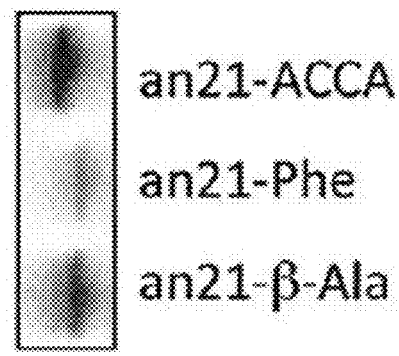
FIG. 3 shows that a linker molecule (an21-ACCA) has been aminoacylated by a flexizyme-catalyzed reaction (Example 1).

As shown in FIG. 3, the results demonstrated that the mobility of the linker molecule of the reaction product is lower than that of the unreacted control linker molecule, indicating that the linker molecule has been aminoacylated by a flexizyme-catalyzed reaction.

[Synthesis of cDNAs]

The cDNAs used for forming peptide-mRNA complexes were prepared by annealing synthetic oligonucleotides by PCR. Synthetic DNAs having the sequences shown below were purchased from Operon Biotechnologies, Inc. (Tokyo). Each cDNA obtained by annealing these oligo DNAs comprises a T7 promoter sequence, a ribosome binding site, a start codon, a peptide aptamer sequence, a spacer peptide sequence (CGSGSGS (SEQ ID NO: 20)), an amber codon and a linker hybridization sequence.

TNF-a_D-Trp.R66:
GCCGCTGCCGCTGCCGCAATGCTTCAGATACAGACAATGCAGACGTTGC
ATATGTATATCTCCTTC

EMP1SS.F63:
GAAGGAGATATACATATGGCAGCAGGTGGTACCTATTCTTCTCATTTTG
GTCCGCTGACCTGG

EMP1SS.R63:
GCCGCTGCCGCTGCCGCATGCTGCACCACCTTGCGGCTTAGAAACCCAG
GTCAGCGGACCAAA

T7g10M.F48:
AATACGACTCACTATAGGGTTAACTTTAAGAAGGAGATATACATATG

CGS3an13.R39:
TTTCCGCCCCCCGTCCTAGCTGCCGCTGCCGCTGCCGCA

CGS3an21.R44:
CCGCCTCCCGCCCCCCGTCCTAGCTGCCGCTGCCGCTGCCGCA

Annealing by PCR was Performed by the Following Procedure.

20 uL of a PCR reaction solution (10 mM Tris-HCl (pH 9.0), 50 mM potassium chloride, 2.5 mM magnesium chloride, 250 μM dNTPs, 0.2% Triton X-100 (Triton X-100, NACALAI TESQUE, INC.) and Taq polymerase) containing 250 nM T7g10M.F48 and TNF-α D-Trp.R66 (or a combination of EMP1SS.F63 and EMP1SS.R63) was prepared and reacted at 94° C. for 1 min, followed by 5 cycles of {50° C. 30 sec, 72° C. 30 sec} using a thermal cycler (TC-3000, Techne). Then, 100 μL of a PCR reaction solution containing 500 nM each of the primers T7g10M.F48 and GCSan21.R44 (or GCSan13.R39) was prepared, and combined with 1 μL of the former PCR reaction product solution, and the mixture was reacted by temperature cycling of 10 cycles of {94° C. 40 sec, 50° C. 40 sec, 72° C. 40 sec}. The reaction product was routinely purified by phenol-chloroform extraction, chloroform extraction, and ethanol precipitation.

[Preparation of mRNAs]

To prepare mRNAs, RNAs were synthesized by transcription reaction using T7 RNA polymerase from the cDNA (TNF-α-DW (an21)) prepared by the procedure described above and the resulting reaction products were routinely purified by phenol-chloroform extraction, chloroform extraction, and 2-propanol precipitation. The purified mRNAs were diluted to a concentration of 10 μM as determined from the UV absorbance at 260 nm.

[Transcription/Translation, Hybridization with the Linkers and Conjugation to a Peptidyl Acceptor]

Translation from mRNAs and complex formation with linker molecules or transcription from cDNAs, translation and complex formation with linker molecules were performed using a reconstituted cell-free translation system.

The reconstituted cell-free translation system used in the present example comprises the following biological polymers: 70S ribosome (1.2 uM), translation initiation factors (IF1 (0.7 uM), IF2 (0.4 uM), IF3 (1.5 uM)), elongation factors (EF-G (0.26 uM), EF-Tu/EF-Ts complex (10 uM)), translation termination factors (RF2 (0.25 uM), RF3 (0.17 uM)), methionyl-tRNA transformylase (MTF (0.6 uM)), ribosome recycling factor (RRF (0.5 uM)), aminoacyl-tRNA synthetases (AlaRS (0.73 uM), ArgRS (0.03 uM), AsnRS (0.38 uM), CysRS (0.02 uM), GlnRS (0.06 uM), GluRS (0.23 uM), GlyRS (0.09 uM), HisRS (0.02 uM), IleRS (0.4 uM), LeuRS (0.04 uM), MetRS (0.03 uM), PheRS (0.68 uM), ProRS (0.16 uM), SerRS (0.04 uM), ThrRS (0.09 uM), TrpRS (0.03 uM), ValRS (0.02 uM), AspRS (0.13 uM), LysRS (0.11 uM), TyrRS (0.02 uM)), creatine kinase (CK, from Roche (4 ug/mL)), myokinase (MK, from Roche (3 ug/mL)), pyrophosphatase (PPa (0.1 uM)), nucleotide diphosphate kinase (NDK (0.1 uM)), T7 RNA polymerase (T7 phage gene-derived recombinant, 0.1 uM)), E. coli tRNA (from Roche, 1.5 mg/mL). The ribosome was purified from E. coli in the logarithmic growth phase, while various proteins other than the ribosome are recombinant proteins expressed and purified from cloned genes for E. coli, unless otherwise specified.

Besides the biological polymers, the following components are included: 50 mM HEPES-KOH (pH7.6), 2 mM NTPs, 20 mM creatine phosphate, 100 mM potassium acetate, 2 mM spermidine, 1 mM dithiothreitol, 6 mM magnesium acetate, 0.1 mM 10-formyl-5, 6, 7, 8-tetrahydrofolic acid.

2.5 µL of a transcription/translation reaction solution was prepared, containing 1.5 µM mRNA or 0.15 µM cDNA, an aminoacyl-initiator tRNA bearing N-chloroacetyl-D-tryptophan (ClAc-D-Trp) as an acyl group (prepared by the procedure disclosed in JPA-2008-125396), and 19 amino acids (each 5 mM) constituting natural proteins except for methionine in addition to the components mentioned above.

In the case where an mRNA is preliminarily prepared by transcription reaction and then translated into a peptide and the resulting peptide is fused to a linker, a peptide-mRNA complex was prepared by the following procedure. First, 4 mM sodium acetate, pH 5.0 and mRNA were mixed in 1:3, and the mixture was heated on a thermoblock at 95° C. for 1 minute and then allowed to stand at room temperature for 5 min. A 25 µM linker solution dissolved in 1 mM sodium acetate was added and the mixture was allowed to stand for 10 minutes to form an mRNA-linker complex. To this were added the other components of the translation system and the mixture was incubated in a constant-temperature water bath (NT-202D, Nissin Scientific Corporation) at 37° C. for 30 minutes, then at room temperature for 12 min, and 0.1 M EDTA (ethylenediaminetetraacetic acid, molecular biology grade, NACALAI TESQUE, INC.) adjusted to pH 7.5 was added at a final concentration of 20 mM, and the mixture was further incubated in the constant-temperature water bath at 37° C. for 30 minutes.

In the case where a cDNA is added to a reaction solution and transcription, translation and fusion to a linker are performed in this reaction solution, a peptide-mRNA complex was prepared by the following procedure. First, a solution containing the components other than the linker was prepared and reacted in a constant-temperature water bath at 37° C. for 30 minutes to perform transcription and translation reactions. To this was added 0.25 µL of 25 µM linker solution, and the mixture was further incubated at 37° C. for 30 minutes, then at room temperature for 12 minutes. Then, 0.1 M EDTA (ethylenediaminetetraacetic acid, molecular biology grade, NACALAI TESQUE, INC.) adjusted to pH 7.5 was added at a final concentration of 20 mM, and the mixture was further incubated in the constant-temperature water bath at 37° C. for 30 minutes.

[Reverse Transcription]

To improve stability of the mRNA moiety of the peptide-mRNA complex, an RNA-DNA hybrid strand was formed by reverse transcription reaction. Specifically, the following procedure was applied. To the translation reaction product described above were added 12 mM Tris-HCl (pH 8.3), 5 µM reverse transcription primer (CGS3an13.R21), 0.5 mM dNTPs, 18 mM Mg (OAc)$_2$, and 10 mM KOH (each expressed by the final concentration). To this was added 1 unit of M-MLV Reverse Transcriptase (RNaseH Minus, Point Mutant, Promega), and the mixture was reacted in a constant-temperature water bath at 42° C. for 10 minutes. Then, EDTA and hydrochloric acid were added at final concentrations of 10 mM and 18 mM, respectively.

[Selection]

The following procedure was taken to assess whether or not the peptide-mRNA complex molecule prepared in this manner is recovered by interaction between the presented peptide and a target protein.

Human tumor necrosis factor-alpha (hereinafter referred to as TNF-α) was chosen as a target protein.

To 6 µL of a cell-free translation reaction product solution containing a peptide-mRNA complex molecule was added biotinylated TNF-α protein at a final concentration of 250 nM, and this solution was transferred to a 0.6 mL ultra-low retention Eppendorf tube (platinum (ultra-low retention) tube, BM Equipment Co., Ltd.), and gently stirred on a rotator (RT-30 mini, Tietech Co., Ltd.) at 4° C. for 1 hr to induce binding. To this solution was added 3 µL of a suspension of streptavidin-immobilized magnetic beads (Dynabeads® Streptavidin M-280, Invitrogen), and the mixture was stirred for further 10 minutes. Then, the magnetic beads were separated by centrifugation and using a magnet holder, and the supernatant was removed, and the pellet was resuspended in 50 µL of TBS (Tris Buffered Saline, 50 mM Tris-HCl (trishydroxymethylaminomethane, NACALAI TESQUE, INC.) pH 7.5, 150 mM sodium chloride) containing 0.05% Tween20 (polyoxyethylene sorbitan monolaurate, NACALAI TESQUE, INC.). This washing process was repeated four times.

Subsequently, 25 µL of PCR (taq-) buffer (10 mM Tris-HCl (pH 9.0), 50 mM potassium chloride, 2.5 mM magnesium chloride, 250 µM dNTPs, 0.25 µM T7g10 m.F48, 0.25 µM CGS3an13.R21, 0.2% Triton X-100) was added to the magnetic beads, and the suspension was heated on a thermoblock at 95° C. for 5 minutes and then the supernatant was collected, whereby a DNA was recovered from the magnetic beads after reverse transcription.

[Quantification by Real-Time PCR]

The amount of the DNA was determined by real-time PCR before the target protein was added and after it was recovered from the magnetic beads. Using LightCycler® 1.5 (Roche Applied Science) as a real-time PCR system, a reaction solution containing Taq polymerase, SYBR® Green I (1:100,000 dilution, Invitrogen), and a test sample solution in the PCR (taq-) buffer described above was assayed.

Model Experiment Targeting TNF-α

TNF-α and a peptide aptamer binding to TNF-α, TNF-α-DW were chosen as a target protein and a peptide aptamer used to test the function of the linkers.

The TNF-α protein used in the present example was a recombinant soluble TNF-α expressed by E. coli. The recombinant TNF-α is a fusion of a sequence of the 77th to 233rd amino acids of wild-type TNF-α to AviTag sequence (GLNDIFEAQKIEWHE (SEQ ID NO: 22)) and Hisx6 tag sequence (SEQ ID NO: 23) at the N-terminus. This protein and a biotin ligase (BirA) using AviTag as a substrate are co-expressed in E. coli, whereby the side chain of the lysine residue of AviTag is biotinylated, so that the TNF-α used in the present example can be readily separated by streptavidin-immobilized beads.

The TNF-α-DW used as a peptide aptamer was a peptide XQRLHCLYLKH (X: Ac-D-Trp (SEQ ID NO: 24)) circularized with a thioether formed by a reaction between the chloroacetyl group of a non-proteinogenic amino acid N-chloroacetyl-D-tryptophan (ClAc-D-Trp) and the thiol group in the side chain of cysteine in the peptide sequence. A cDNA encoding a sequence containing a spacer amino acid sequence CGSGSGS (SEQ ID NO: 20) fused to the C-terminus of this peptide was prepared by the method described above to form a peptide-mRNA complex molecule in a cell-free transcription/translation system.

Figure 4:
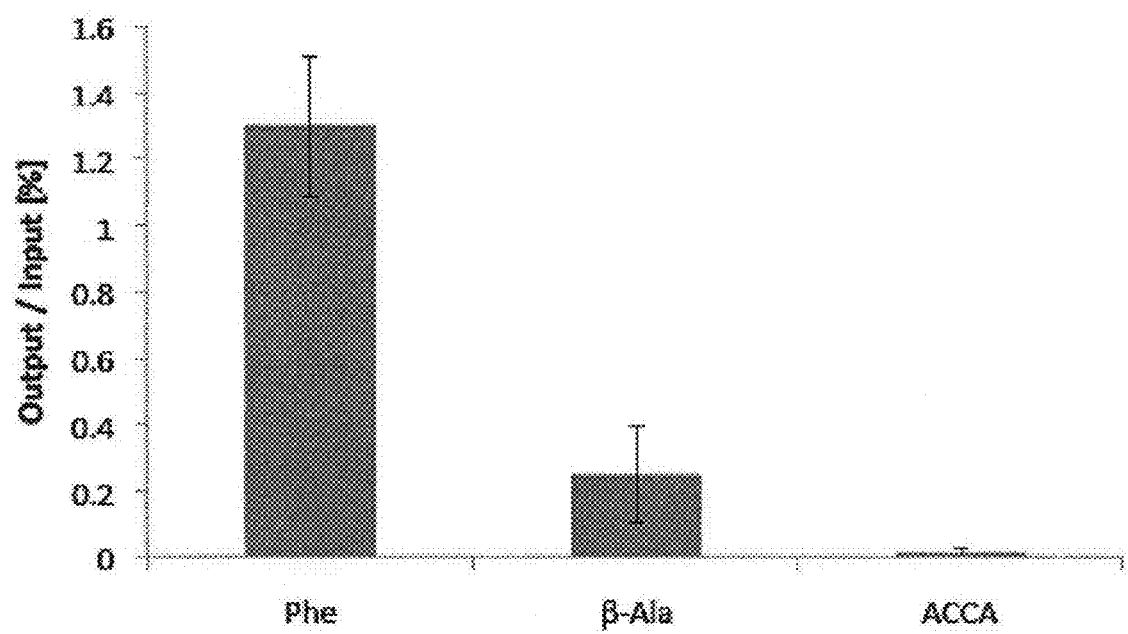
FIG. 4 shows the yields of complexes of a peptide aptamer (TNF-α-DW) and an mRNA when the mRNA was added to the reaction solution (Example 1).
Figure 5:
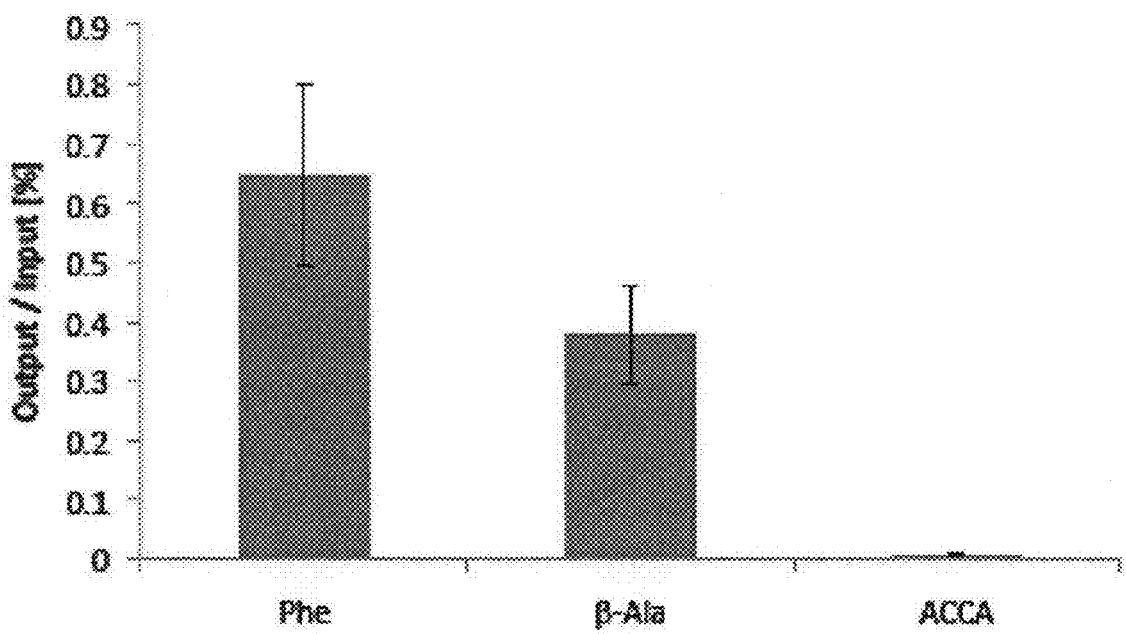
FIG. 5 shows the yields of complexes of a peptide aptamer (TNF-α-DW) and an mRNA when a cDNA was added to the reaction solution (Example 1).

The yields of peptide-mRNA complexes using a combination of this peptide aptamer and the target protein are shown in FIG. 4 and FIG. 5. The yields with an21-Phe, that is a linker having L-phenylalanine attached to the 3' end via an ester and an2113-Ala were 1.30% and 0.25% when the mRNA was added to the translation reaction solution (FIG. 4), or 0.65% and 0.38% when a cDNA was added (FIG. 5). However, the yield with the an21-ACCA linker unmodified at the 3' end was about several tens of times lower than those obtained with the modified linkers (0.015% in the case of mRNA, or 0.007% in the case of cDNA), showing that peptide-mRNA complex molecules are efficiently recovered by conjugating L-phenylalanine or β-L-alanine to the C-terminus of the peptide synthesized by translation via a covalent bond.

Example 2

Verification of Mapping Between the Presented Peptide and the mRNA

In the foregoing experiments using a single type of the presented peptide and the mRNA encoding its sequence, one cannot exclude the possibility that another linker molecule binds to the peptide synthesized by translation from the mRNA as an acceptor or the possibility that the linker molecule and mRNA molecule forming a double strand are replaced by another linker molecule or mRNA during the manipulation. Thus, the following experiments were performed to verify that mapping between the peptide presented by recovered peptide-mRNA-linker complex molecules and the mRNA has been exactly made.

Figure 6:
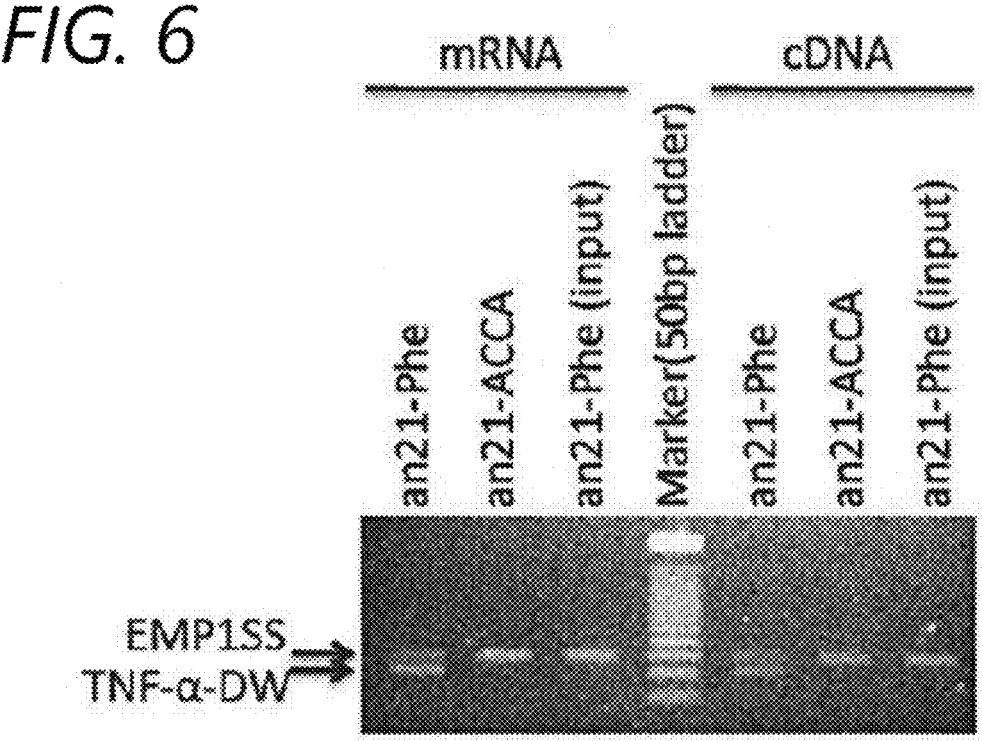
FIG. 6 shows the result confirming that the peptide-mRNA complex presenting TNF-α-DW was recovered more efficiently than a control (EMP1SS) complex unbounded to the target (Example 2).

First, an mRNA or cDNA encoding a peptide sequence that does not bind to the target protein (EMP1SS: XAAGG-TYSSHFGPLTWVSKPQGGAA (SEQ ID NO: 25), wherein X is Ac-D-Trp similarly to TNF-α-DW) as a control of TNF-α-DW was prepared by the procedure shown in Example 1, and mixed with an mRNA or cDNA encoding TNF-α-DW in a molar ratio of 100:1. This mixture was used to perform experiments similar to those described above, and the recovered DNA was amplified by PCR under the following conditions. That is, 20 µL of a reaction solution containing Taq polymerase and a test sample solution in PCR (taq-) buffer was prepared and reacted by temperature cycling of 30 cycles of {94° C. 40 sec, 61° C. 40 sec, 72° C. 40 sec} (with a slope of 0.5° C./sec from 61° C. to 72° C.) using a thermal cycler. 2.5 µL of the reaction product solution was separated by electrophoresis using a gel consisting of TAE (40 mM Tris-acetate, 1 mM EDTA) and 3% agarose (low electroendosmosis, NACALAI TESQUE, INC.), and electrophoretograms were obtained under a transilluminator after staining with ethidium bromide. The results are shown in FIG. 6.

A band derived from the mRNA encoding TNF-α-DW is observed at the position of about 90 bp, while a band derived from the mRNA encoding the control EMP1SS is observed at the position of about 150 bp. When the an21-ACCA linker containing no peptidyl acceptor was used, only a band derived from the mRNA of EMP1SS was observed, reflecting the molar ratio of the two types of cDNA in the initial mixture. With an21-Phe, however, a band derived from the mRNA of TNF-α-DW was observed with a fluorescent intensity comparable to or higher than that of EMP1SS. Thus, it was demonstrated that peptide-mRNA complexes presenting TNF-α-DW that binds to the target protein were recovered more efficiently than peptide-mRNA complexes presenting EMP1SS that does not bind to the target. This indicates that mapping between the peptide presented by peptide-mRNA-linker complex molecules and the mRNA does not change during the experiments. In addition, this result was equally obtained either when peptide-mRNA complexes were formed by adding the mRNAs into the translation reaction solution or peptide-mRNA complexes were formed by adding cDNAs.

Example 3

Selection of a TNF-α-DW-Spiked Library
[Random Peptide Library]
Evaluation was made to determine whether or not an mRNA or cDNA encoding a low copy number peptide aptamer contained in an mRNA library encoding random peptide sequences can be selected by repeating selection multiple times.

First, a peptide aptamer library presenting a random sequence of 8-12 amino acids was prepared. This library was prepared as an mRNA encoding the random sequence. This library has a similar structure to those of the preparations described above except that the sequence region presenting TNF-α-DW or EMP1SS is randomized and the region with which the linker hybridizes to form a double strand has a length of 13 bp.
[Preparation of a TNF-α-DW-Spiked Library]
A spiked library was prepared by mixing an mRNA encoding TNF-α-DW (TNF-α-DW (an13): the region forming a double strand with the linker has a length of 13 bp) with this random peptide library in a molar ratio of 1,000, 000:1.
[Round 1]
This spiked mRNA library and an21-Phe linker was used to perform translation and peptide-mRNA complex formation following the procedures shown in Examples 1 and 2 above (round 1).

Negative selection was performed in which a peptide-mRNA complex solution was mixed with unbound streptavidin-immobilized magnetic beads at 4° C. for 10 minutes, whereby peptide-mRNA complexes binding to the magnetic beads were eliminated. To this solution was added TNF-α at a final concentration of 250 nM, and mixed at 4° C. for 1 hour. Streptavidin-immobilized magnetic beads were added to this solution, and bound at 4° C. for 10 minutes and washed with TB ST four times.

Then, the washed magnetic beads were suspended in 10 µL of a reverse transcription reaction solution (5 units/µL M-MLV Reverse Transcriptase (Promega), 2 µM CGS3an21.R44, 0.5 mM dNTP, 10 mM Tris-HCl (pH 8.3), 15 mM potassium chloride, 0.6° C. mM magnesium chloride, 2 mM dithiothreitol), and the suspension was warmed at 42° C. for 1 hr to perform reverse transcription reaction. Subsequently, 15 µL of PCR (taq-) buffer (containing 0.25 µM T7g10 m.F48 and 0.25 µM CGS3an21.R44 as primers) was added to the suspension of the magnetic beads, and the mixture was heated on a thermoblock at 95° C. for 5 minutes and then the supernatant was collected, whereby a DNA was recovered from the magnetic beads after reverse transcription.

An aliquot each of the mRNA immediately after translation and the recovered DNA was assayed for the copy number by real-time PCR in the same manner as in Example 1. Further, amplification by PCR was performed in the same manner as in Example 2 and terminated before the amplification reaction reached saturation to avoid reannealing of the reaction products to each other.

[Rounds 2, 3 and 4]

In round 2 and the subsequent rounds, the results were compared in the case where an mRNA synthesized from the PCR product of the previous round was used for translation reaction or the cDNA obtained as the PCR product of the previous round was used to perform transcription and translation reactions at the same time. Experimental procedures were similar to those of Examples 1 and 2 except that negative selection was performed multiple times. Specifically, the number of times of negative selection increases by one in each round. In round 2 and the subsequent rounds, PCR amplification was also terminated before the amplification reaction reached saturation.

[Identification of Selected Sequences]

Figure 7:
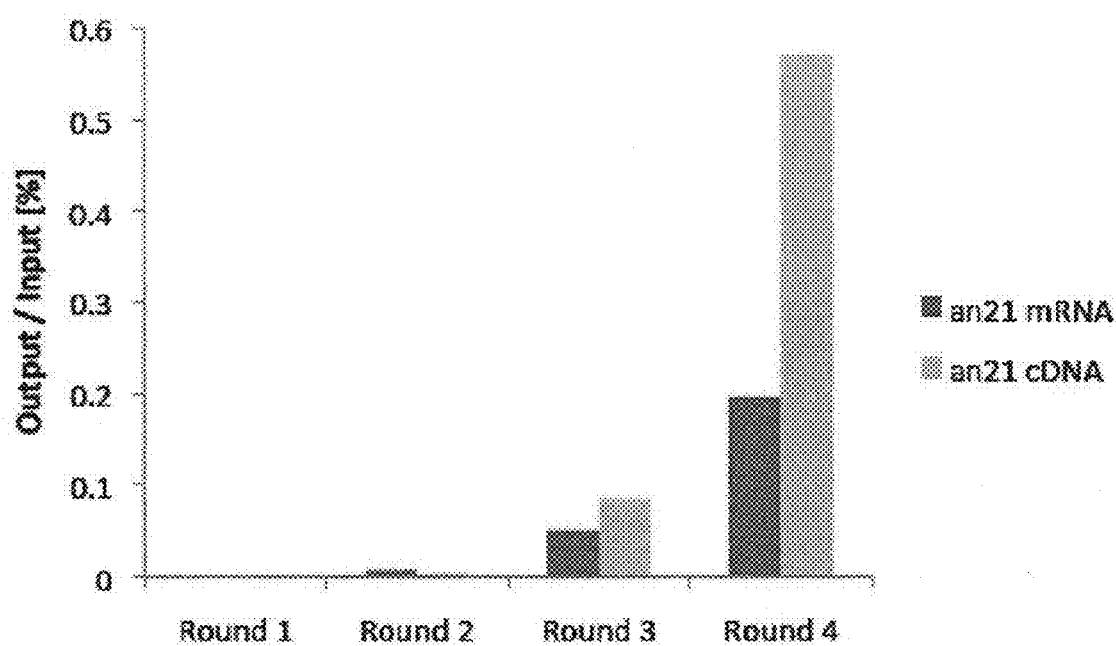
FIG. 7 shows changes in binding affinity with the number of rounds when a peptide aptamer was selected by repeating selection multiple times using a TNF-α-DW-spiked library and an21-Phe linker (Example 3).

After the operation of round 2 was repeated multiple times, a great increase in binding affinity was observed in round 4. Changes in binding affinity with the number of rounds are shown in FIG. 7. The PCR products were routinely cloned using pGEM-T easy Vector System I (Promega), and 5 clones each were analyzed by DNA sequencing. The results showed that all the resulting clones had the same sequence as that of TNF-α-DW (an21).

It was demonstrated that peptide aptamers can be selected from peptide libraries consisting of random sequences by this method.

SEQUENCE LISTING FREE TEXT
  SEQ ID NO: 1: Synthetic oligonucleotide
  SEQ ID NO: 2: Synthetic oligonucleotide
  SEQ ID NO: 3: Flexizyme Fx
  SEQ ID NO: 4: Flexizyme eFX
  SEQ ID NO: 5: Flexizyme dFx
  SEQ ID NO: 6: Synthetic oligonucleotide
  SEQ ID NO: 7: Synthetic oligonucleotide
  SEQ ID NO: 8: Synthetic oligonucleotide TNF-α D-Trp.R66
  SEQ ID NO: 9: Synthetic oligonucleotide EMP1SS.F63
  SEQ ID NO: 10: Synthetic oligonucleotide EMP1SS.R63
  SEQ ID NO: 11: Synthetic oligonucleotide T7g10M.F48
  SEQ ID NO: 12: Synthetic oligonucleotide CGS3an13.R39
  SEQ ID NO: 13: Synthetic oligonucleotide CGS3an21.R44
  SEQ ID NO: 14: Synthetic oligonucleotide CGSan13.R21
  SEQ ID NO: 15: TNF-alpha-DW (an21)
  SEQ ID NO: 16: TNF-alpha-DW (an13)
  SEQ ID NO: 17: EMP1SS (an21)
  SEQ ID NO: 18: TNF-alpha
  SEQ ID NO: 19: Flexizyme aFx.

(Notes) In the DNAs of SEQ ID NOs: 15-17, the codon for methionine is assigned to a non-proteinogenic amino acid (ClAc-D-Trp) (genetic code reprogramming).

The invention claimed is:

1. A process for preparing an [mRNA]-[linker]-[peptide] conjugate in which an mRNA and a peptide as a translation product thereof are coupled via a linker in a reconstituted in vitro protein synthesis reaction solution, which comprises hybridizing, in the reconstituted in vitro protein synthesis reaction solution, the linker to the mRNA without first ligating the linker to the mRNA; and translating, in the reconstituted in vitro protein synthesis reaction solution, the mRNA without first ligating the linker to the mRNA, wherein said mRNA comprises a sequence encoding the peptide sequence and 3' end region downstream thereof, and wherein said linker comprises a chimeric oligonucleotide consisting of a single-stranded structure region that hybridizes with the 3'-end region of the mRNA sequence; said single-stranded structure region is attached at its 3'-end to the 5' end of an oligo RNA having the sequence 5'-ACCA-3' via a polyethylene glycol moiety; and an amino acid attached to the 3'-O of ribose of the 3'-terminal adenosine of the oligo RNA via an ester bond.

2. The process of claim 1, which further comprises introducing a template DNA for the mRNA into the reconstituted in vitro protein synthesis reaction solution and transcribing the DNA into the mRNA.

3. The process of claim 1, wherein the reconstituted in vitro protein synthesis reaction solution contains a tRNA charged with a non-proteinogenic amino acid or hydroxy acid.

4. The process of claim 1, which comprises adding the linker and mRNA to the reconstituted in vitro protein synthesis reaction solution before peptide chain elongation.

5. A method for selecting a peptide aptamer that binds to a target substance from a library of [mRNA]-[linker]-[peptide] conjugates in which each mRNA and a peptide as a translation product thereof are coupled via a linker, said method comprising:

preparing a library of [mRNA]-[linker]-[peptide] conjugates conjugates using the method of claim 1;

contacting the target substance with the library of [mRNA]-[linker]-[peptide] conjugates; and selecting a conjugate presenting the peptide bound to the target substance.

6. The process of claim 5, which comprises adding the linker and mRNA to the reconstituted in vitro protein synthesis reaction solution before peptide chain elongation.

7. The process of claim 5, which further comprises introducing a template DNA for the mRNA into the reconstituted in vitro protein synthesis reaction solution and transcribing the DNA into the mRNA.

8. The process of claim 5, wherein the reconstituted in vitro protein synthesis reaction solution contains a tRNA charged with a non-proteinogenic amino acid or hydroxy acid.

9. The process of claim 5, wherein said target substance is biotinylated.

* * * * *